United States Patent
Dengler et al.

(10) Patent No.: US 10,575,627 B2
(45) Date of Patent: Mar. 3, 2020

(54) BRUSH HEAD ASSEMBLY AND METHODS OF MANUFACTURE

(71) Applicant: KONINKLIJKE PHILIPS N.V., Eindhoven (NL)

(72) Inventors: Evan Dak Wah Dengler, Seattle, WA (US); Michael Schmitt, Portland, OR (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/573,950

(22) PCT Filed: May 9, 2016

(86) PCT No.: PCT/IB2016/052622
§ 371 (c)(1),
(2) Date: Nov. 14, 2017

(87) PCT Pub. No.: WO2016/181278
PCT Pub. Date: Nov. 17, 2016

(65) Prior Publication Data
US 2018/0289140 A1    Oct. 11, 2018

Related U.S. Application Data

(60) Provisional application No. 62/161,348, filed on May 14, 2015.

(51) Int. Cl.
*A46B 3/10* (2006.01)
*A46B 3/20* (2006.01)
(Continued)

(52) U.S. Cl.
CPC .................. *A46B 3/10* (2013.01); *A46B 3/20* (2013.01); *A46B 7/00* (2013.01); *A46B 9/08* (2013.01); *A46D 3/047* (2013.01); *A61C 17/22* (2013.01)

(58) Field of Classification Search
CPC .... A46B 3/00; A46B 3/06; A46B 3/08; A46B 3/10; A46B 3/20; A46B 9/08; A46D 3/00; A46D 3/04; A46D 3/045
(Continued)

(56) References Cited

U.S. PATENT DOCUMENTS 5,474,366 A    12/1995   Zahoransky et al.
5,802,656 A    9/1998    Dawson et al.
(Continued)

FOREIGN PATENT DOCUMENTS

EP    1593321 A1    11/2005
EP    2708155 A1    3/2014
(Continued)

OTHER PUBLICATIONS

Machine Translation of WO 2004080238.*

*Primary Examiner* — David Redding

(57) ABSTRACT

A brush head (32) including a neck (40) having a brush neck (42); a plurality of bristle tufts (21), each of which includes a plurality of bristle strands with a free end (25) and a proximal end (23), the proximal end having a proximal end head portion (26); a plurality of retention rings (50), each configured to receive the proximal end of at least one of the plurality of bristle tufts; an elastomeric matrix (30) bonded to at least a portion of the brush neck, the plurality of retention rings, and the proximal end of the plurality of bristle tufts, wherein the proximal end head portion of each of the plurality of bristle tufts is configured to comprise a space (27) between the proximal end head portion and the respective retention ring.

15 Claims, 6 Drawing Sheets

(51) Int. Cl.
*A46B 7/00* (2006.01)
*A46B 9/08* (2006.01)
*A46D 3/04* (2006.01)
*A61C 17/22* (2006.01)

(58) Field of Classification Search
USPC .............................................. 15/167.1, 201
See application file for complete search history.

(56) References Cited

U.S. PATENT DOCUMENTS

| | | | |
|---|---|---|---|
| 5,970,564 | A | 10/1999 | Inns et al. |
| 6,088,870 | A | 7/2000 | Holbein |
| 6,406,099 | B2 | 6/2002 | Boucherie |
| 6,553,604 | B1 | 4/2003 | Braun et al. |
| 6,952,854 | B2 | 10/2005 | Blaustein et al. |
| 7,281,768 | B2 | 10/2007 | Sato et al. |
| 7,549,187 | B2 * | 6/2009 | Pfenniger ................ A46B 3/06 15/110 |
| 7,600,288 | B1 | 10/2009 | Givonetti |
| 7,992,247 | B2 | 8/2011 | Pfenniger et al. |
| 8,069,524 | B2 | 12/2011 | Kraemer |
| 8,099,819 | B2 | 1/2012 | Kraemer |
| 2001/0024060 | A1 | 9/2001 | Boucherie |
| 2001/0038237 | A1 | 11/2001 | Boucherie |
| 2003/0041402 | A1 | 3/2003 | Stein et al. |
| 2007/0006410 | A1 | 1/2007 | Kraemer |
| 2007/0271717 | A1 * | 11/2007 | Clos ........................ A46B 3/20 15/167.1 |
| 2008/0168613 | A1 * | 7/2008 | Kraemer ................. A46B 9/12 15/167.1 |
| 2009/0083925 | A1 * | 4/2009 | Mathiez ................. A46B 3/005 15/207.2 |
| 2011/0167579 | A1 | 7/2011 | Huber et al. |
| 2012/0233790 | A1 | 9/2012 | Uchida et al. |
| 2013/0241267 | A1 | 9/2013 | Kumph |
| 2014/0232173 | A1 | 8/2014 | Birk et al. |

FOREIGN PATENT DOCUMENTS

| | | | | |
|---|---|---|---|---|
| EP | 2810580 A1 | 12/2014 | | |
| WO | 2004080238 A1 | 9/2004 | | |
| WO | WO-2004080238 A1 * | 9/2004 | ............... | A46B 3/06 |
| WO | 2006109077 A1 | 10/2006 | | |

* cited by examiner

BRUSH HEAD ASSEMBLY AND METHODS OF MANUFACTURE

CROSS-REFERENCE TO PRIOR APPLICATIONS

This application is the U.S. National Phase application under 35 U.S.C. § 371 of International Application No. PCT/IB2016/052622, filed on May 9, 2016, which claims the benefit of U.S. Provisional Patent Application No. 62/161,348, filed on May 14, 2015. These applications are hereby incorporated by reference herein.

FIELD OF THE INVENTION

The present disclosure is directed generally to a brush head assembly with bristle tufts retained within an elastomeric matrix, as well as to methods for manufacturing the brush head assembly.

BACKGROUND

Periodontal diseases are thought to be infectious diseases caused by bacteria present in dental plaques. Tooth brushing is a highly effective method to remove dental plaque from the teeth. Power toothbrushes can enhance the removal of dental plaque. Such power toothbrushes have a set of bristles attached to a brush head which is moved by a driver that causes the bristles to scrub dental surfaces.

The brush heads of both manual and power toothbrushes comprise bristles which are used to clean the teeth, tongue, and cheeks. In some toothbrushes, the bristles are organized into bristle tufts contained within retention rings. The retention rings serve to secure the bristle tufts within the brush head and often have a hollow circular shape with an interior and exterior circular circumference. During manufacture, the bristle tufts are inserted into the hollow interior of the retention ring, and the bristles are then fused together using heat to form a head which cannot be pulled out through the retention ring.

Often, however, the retention rings are not firmly secured within the brush head. As a result, the ring and bristle tuft can be or become loose within the brush head, and the bristles might not always be positioned at an angle optimal for brushing. As such, under the dynamic conditions of motion induced by the power toothbrush operation, for example, the bristle tuft structure can undergo higher stresses under the dynamic motion, which could lead to separation. Further, the process of organizing the bristles into tufts within the retention rings and then cooling the brush head material, or allowing it to cool, in order to fix the tufts in place can be time-consuming and expensive.

Accordingly, there is a need in the art for brush head assemblies, and methods of their manufacture, that permanently and efficiently retain bristle tufts within the brush head.

SUMMARY OF THE INVENTION

The present disclosure is directed to inventive methods for manufacturing a brush head with secured bristle tufts. Various embodiments and implementations herein are directed to manufacturing methods in which bristle tufts are affixed with retention rings and are then embedded within an elastomeric matrix resulting in a completed brush head. Using the various embodiments and implementations herein, cost-effective and efficient production of brush heads with secured bristle tufts is substantially improved. For example, in some embodiments, the manufacturing method results in a brush head with the head of the bristle tuft embedded in the elastomeric matrix and spaced from the retention ring. As a result, in the finished brush head there is elastomeric matrix located between the retaining ring and the tuft ring. When the bristle tuft is pulled, some of the force is distributed to the surrounding elastomeric matrix located between the head of the bristle tuft and the retention ring. This provides for greater flexibility of tuft movement, and also, by reducing the pressure, reduces the probability of the retaining head breaking through the retaining ring, causing premature brush head failure due to bristle tuft loss.

Generally in one aspect, a brush head is provided. The brush head includes: a hard brush neck; a plurality of bristle tufts, each of which comprises a plurality of bristle strands having a free end and a proximal end, the proximal end comprising a proximal end head portion; a plurality of retention rings, each configured to receive the proximal end of at least one of the plurality of bristle tufts; an elastomeric matrix bonded to at least a portion of the hard brush neck, the plurality of retention rings, and the proximal end of the plurality of bristle tufts, where the proximal end head portion of each of the plurality of bristle tufts is configured to comprise a space between the proximal end head portion and the respective retention ring.

According to an embodiment, the plurality of retention rings is at least partially interconnected by a network of webbing.

According to an embodiment, the network of webbing is at least partially encompassed within the elastomeric matrix.

According to an embodiment, the elastomeric matrix completely encompasses the hard brush neck and the proximal end head portion of each of the plurality of bristle tufts.

According to an embodiment, the bristle strands are made of nylon, and the elastomeric matrix comprises a flexible thermoplastic elastomer.

According to an aspect is a method for manufacturing a brush head. The method includes the steps of: providing a plurality of retention rings and a plurality of bristle tufts, wherein each of the plurality of bristle tufts comprises a plurality of bristle strands having a free end and a proximal end; inserting at least one of the plurality of bristle tufts into a respective one of the plurality of the retention rings; applying heat to each of the bristle tuft proximal ends at a temperature and distance sufficient to at least partially melt the bristle tuft proximal end to create a proximal end head portion; creating a first space between the each of the proximal end head portions and the respective retention ring; positioning a brush neck in relation to the proximal end head portions, wherein the positioning of the brush neck defines a second space in relation to the proximal end head portions; and injecting a thermoplastic elastomer to create an elastomeric matrix that at least partially encompasses the brush neck, the plurality of retention rings, the proximal end head portions, wherein the elastomeric matrix fills the first and second spaces.

According to an embodiment, the creating step comprises applying a force to the free end of each of the plurality of bristle tufts.

According to an embodiment, the creating step comprises using a guide to create the first space.

According to an aspect is a brush head assembly for a power toothbrush. The brush head assembly includes a neck and a brush head, the brush head comprising: a plurality of retention rings each containing a bristle tuft, each bristle tuft comprising a proximal end head portion at a proximal end thereof, the proximal end head portion separated from a respective one of the retention rings by a first space; a brush neck positioned relative to the plurality of proximal end head portions to create a second space; an elastomeric matrix encompassing at least a portion of the plurality of retention rings, the proximal end head portions, and the brush neck, wherein the elastomeric matrix fills the first and second spaces.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a brush head assembly with bristle tufts retained within an elastomeric matrix, and methods of their manufacture. More generally, Applicants have recognized and appreciated that it would be beneficial to provide a brush head formed with bristles embedded in an elastomeric matrix in order to improve bristle retention. Embedding bristle tufts within an elastomeric matrix such that the head of the bristle tuft is spaced from the retention ring provides for higher tuft retention, which is beneficial to a brush head's function, especially in powered toothbrush devices. A particular goal of utilization of certain embodiments of the present disclosure is the ability to efficiently manufacture brush heads with improved retention of the bristle tuft and improved bristle tuft flexibility.

The brush heads disclosed and described herein can be used with any manual or power toothbrush device. One example of a power toothbrush device that the brush head can be used with Sonicare® devices available from Koninklijke Philips Electronics N.V. This oral care device is based upon an actuator with a reciprocating brush head including bristles to provide an effective cleaning of a user's teeth.

Figure 1:
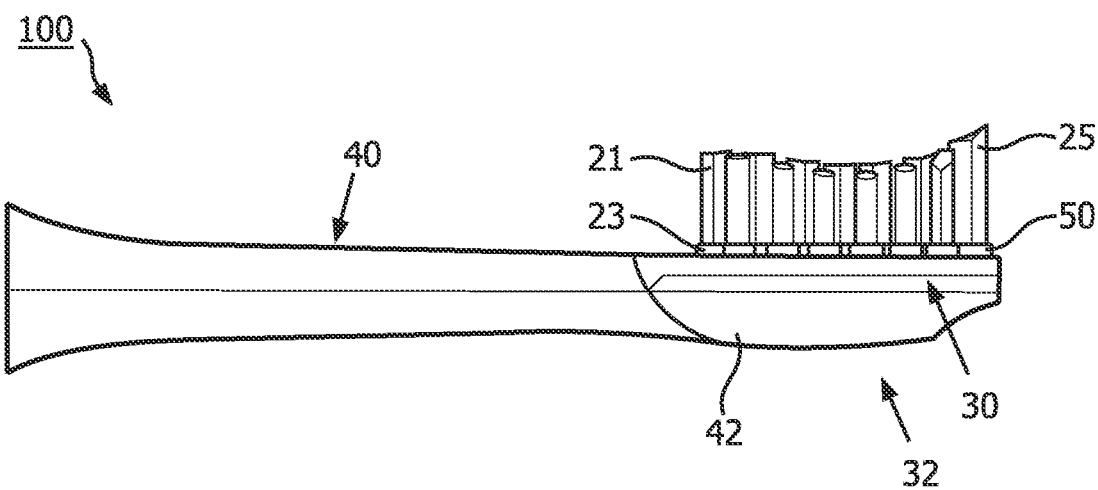
FIG. 1 is a schematic representation of a side view of a brush head assembly in accordance with an embodiment.

Referring to FIG. 1, in one embodiment, a schematic representation of a brush head assembly 100 is provided. The brush head assembly includes a neck 40, which can be coupled to any manual brush shaft, or, more preferably, to any actuator and drive shaft (not shown) made or suitable for oral care devices now known or to be developed. The brush head 32 of the brush head assembly includes a plurality of bristle tufts 21, each of which comprises a plurality of bristle strands. According to an embodiment, the bristle tufts are composed of nylon, or another suitable material, and optionally can be coated with polyurethane, polybutylene terephthalate (PBT), polyolefin, combinations of these, or a similar polymer. Each bristle tuft includes a proximal end 23 and a free end 25, where the proximal end of each bristle tuft is retained within the brush head assembly 100. Each bristle tuft 21 is retained within a retention ring 50. The proximal end of the bristle tuft and the retention rings and the portion of the neck that is the brush neck 42 are retained within a flexible elastomeric matrix 30 to form a head portion 32 of the brush head assembly 100. According to an embodiment, the elastomeric matrix 30 is preferably made from a flexible thermoplastic elastomer (TPE), and the retention rings are preferably made from thermoplastic polymer such as polypropylene. Each of the neck 40, brush neck 42, and the retention rings 50 is preferably made from a material with a higher elastic modulus value than the elastomeric matrix 30.

Figure 2:
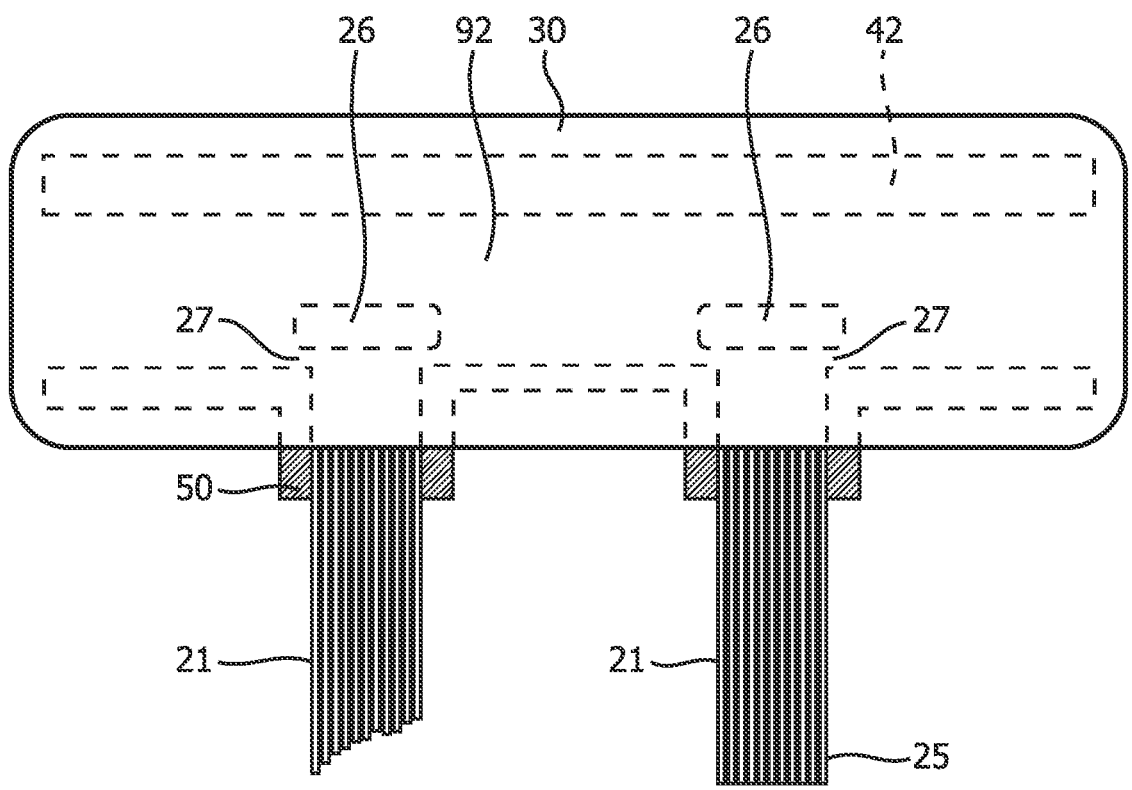
FIG. 2 is a schematic representation of a portion of a brush head assembly in accordance with an embodiment.
Figure 4:
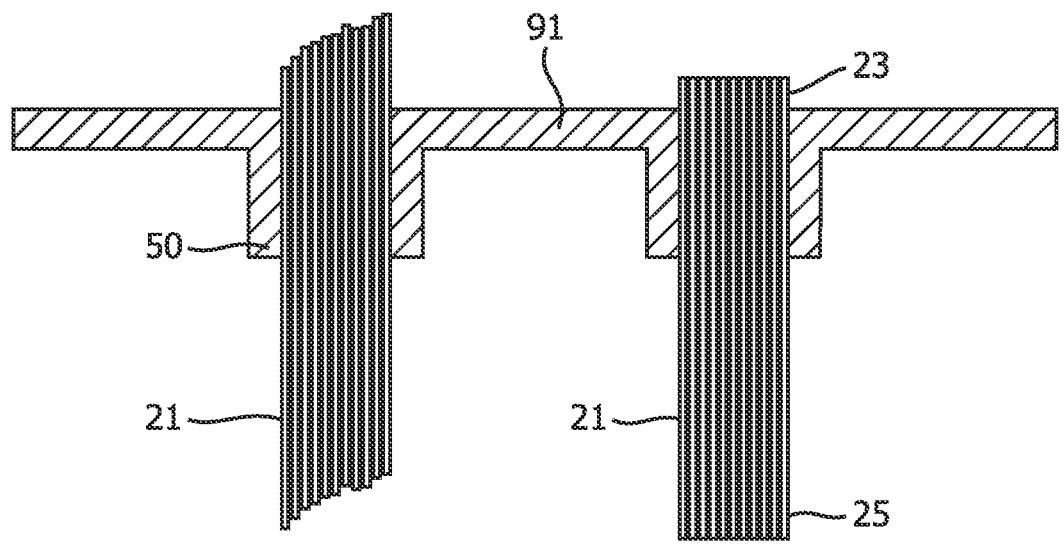
FIG. 4 is a schematic representation of a brush head during manufacturing, in accordance with an embodiment.

Referring to FIG. 2, in one embodiment, is a cut-away view of a portion of the brush head 32. Each of the bristle tufts 21 is surrounded by a retaining ring 50, or a portion of a retaining ring 50, and each has a free end 25 and a proximal end 23 with a head portion 26. According to an embodiment, a plurality of retention rings 50 is provided. Retention rings 50 can be of a plurality of shapes, sizes, configurations or tapers. For example, the retention rings 50 can be connected or at least partially interconnected by a webbing or network of webbing links 91 to improve retention ring and bristle tuft retention within the brush head (as shown in FIG. 4), although a webbing link is not necessary and a plurality of individual retention rings 50 can be used. It can be appreciated that while the retaining rings 50 shown in the figures herein are shown as straight cylinders for the sake of simplicity, they can be a variety of different shapes both inside and outside (pentagons, squares, etc.) and have various tapers or partial tapers to the inside and outside of the retaining rings, and retaining rings of various shapes can be used together in a single brush head.

An elastomeric material is formed around the brush neck 42, the proximal end head portion 26 of the bristle tufts 21, all or a portion of the retaining rings 50, as well as the webbing links 91 if they are present. The elastomeric material forms an elastomeric matrix 30 that fills in the space 92 between the brush neck 42 and the proximal end head portion 26, as well as the gap 27 between the proximal end head portion 26 and the retaining rings 50. According to an embodiment, elastomeric matrix 30 is preferably made from a flexible thermoplastic elastomer, while the retaining rings are preferably made from thermoplastic polymer such as polypropylene. According to this embodiment, each of the brush neck 42 and the retaining rings 50 is made from a material with a higher elastic modulus than the elastomeric matrix 30. As a result there is flexible elastomeric matrix between the retaining head and the tuft ring. This additional layer of elastomeric matrix between the retaining head and the tuft ring can be compressed during operation, such that when the bristle tuft is being pulled downward toward the free end of the bristles the matrix absorbs some of the pressure, and the force is distributed throughout the elastomeric matrix. This results in greater flexibility of tuft movement, and also, by reducing the pressure, reduces the probability of the retaining head breaking through the retaining ring.

Figure 3:
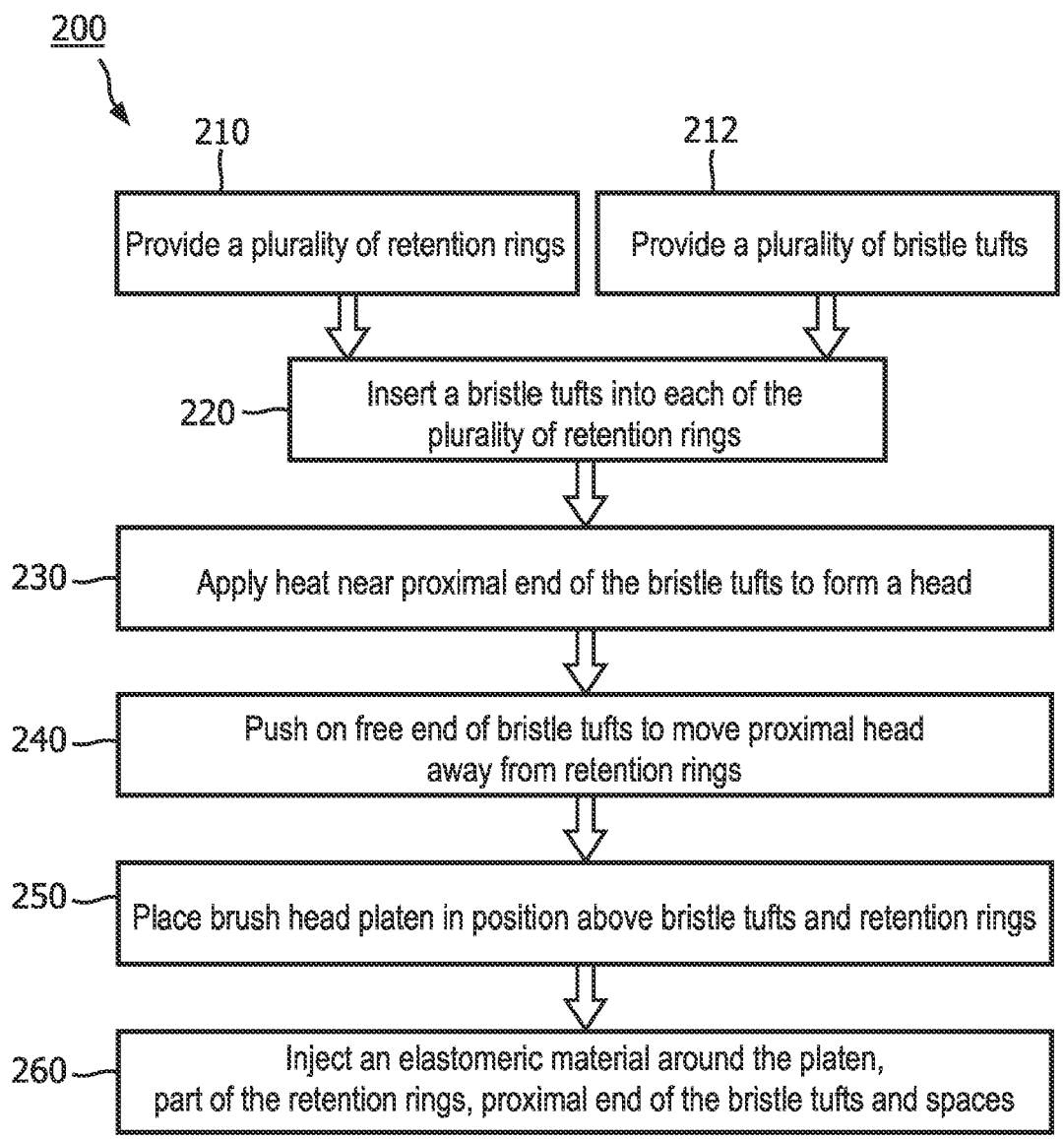
FIG. 3 is a flowchart of a method for manufacturing a brush head assembly with bristle tufts retained within an elastomeric matrix in accordance with an embodiment.

Referring to FIG. 3, in one embodiment, is a method 300 for manufacturing a brush head 32. The brush head can be any of the brush heads described or otherwise envisioned herein. For example, brush head 32 can comprise a plurality of bristle tufts 21, each retained within a retention ring 50 and each having a proximal end 23 and a free end 25, where the proximal end of each bristle tuft is retained within a flexible elastomeric matrix 30 to form a head portion 32 of the brush head assembly 100. According to an embodiment, the proximal end head portions 26 of the bristles are spaced a short distance from the retaining rings 50, resulting in a gap or space 27 which comprises the elastomeric matrix 30. Many other embodiments and configurations of the brush head 32 are possible.

In step 210 of the method, a plurality of retention rings 50 is provided. According to an embodiment, the retention rings can be made from thermoplastic polymer such as polypropylene. The retention rings 50 ban be made from a material with a higher elastic modulus value than, for example, the elastomeric matrix 30. The retention rings can be of a plurality of shapes, sizes, configurations, or tapers. According to an embodiment, the retention rings are connected or at least partially interconnected by a webbing or network of webbing links 91 to improve retention ring and bristle tuft retention within the brush head.

In step 212 of the method, a plurality of bristle tufts 21 each comprising a plurality of bristle strands is provided. Each bristle tuft includes a proximal end 23 and a free end 25, where the proximal end of each bristle tuft is retained within the brush head assembly 100.

In step 220 of the method, each of the plurality of bristle tufts 21 is inserted into a respective one of the plurality of retention rings 50. This can be, for example, an automated process in which bristle tufts are sequentially inserted into the retention rings, are inserted into the retention rings in a random order, or are simultaneously inserted into the retention rings. Referring to FIG. 4, in one embodiment, is a schematic representation of the bristle tufts 21 inserted into the retention rings 50, which in this embodiment are organized into a network 91. The bristles of the bristle tufts may be inserted to comprise different heights and different angles, and can vary among a single bristle tuft or between different bristle tufts.

Figure 5:
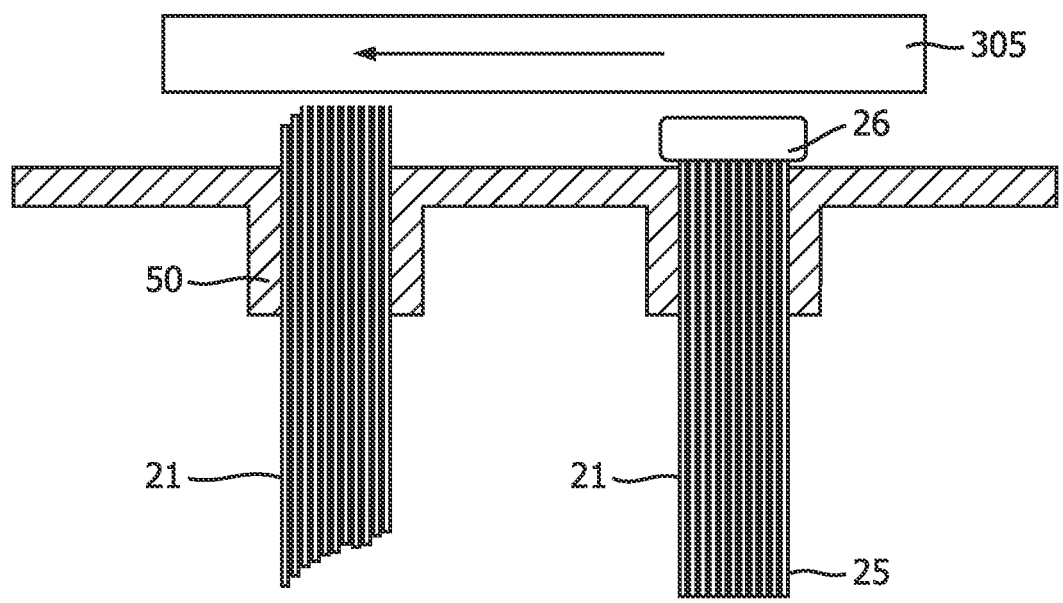
FIG. 5 is a schematic representation of a brush head during manufacturing, in accordance with an embodiment.

At step 230 of the method, heat is applied near the proximal end 23 of the plurality of bristle tufts 21 to create a proximal end head portion 26 on each of the tufts 21. Proximal end head portion 26 is the melted ends of the bristle tuft 21. The heat can be supplied by a heat source that comes into direct physical contact with the proximal end 23 of the bristle tufts, or the heat can be supplied by heated air or any of a variety of other heat sources. As shown in FIG. 5, for example, a hot knife 42 is moved across the brush head being manufactured at a distance from the proximal end 23 of the plurality of bristle tufts. The distance is determined based on a variety of factors, including but not limited to, the materials of the bristles and retention rings, the temperature of the hot knife, the moving speed of the hot knife and the material of the hot knife. The optimal factors will achieve melting of the bristle tufts 21 to form a proximal end head portion 26, but not so as to melt the retaining rings, or bind the proximal end head portion 26 to the retaining rings.

Figure 6:
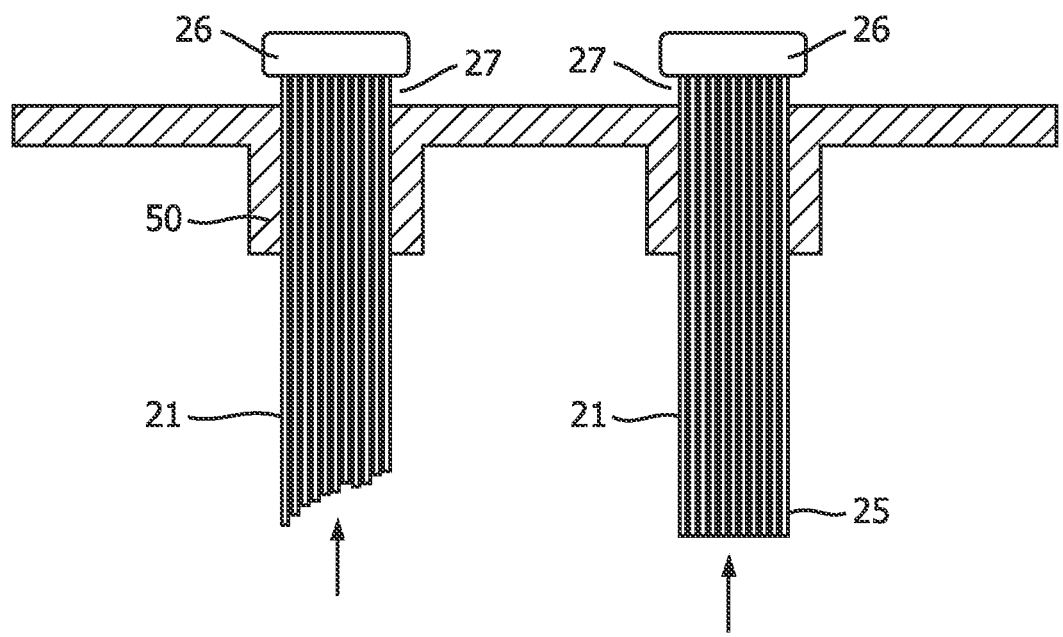
FIG. 6 is a schematic representation of a brush head during manufacturing, in accordance with an embodiment.

In step 240 of the method, a space or gap 27 is created between the proximal end head portion 26 of each bristle tuft and the tuft retention ring 50 surrounding that bristle tuft. This space can be created in a variety of ways. For example, step 240 can be effectively accomplished during steps 220 and 230 by pushing the bristle tufts sufficiently far into the retention rings and then melting just the proximal end head portion 26 of the bristle tufts such that there is a space or gap between the newly-created head portion and the retention rings. According to another embodiment, a force can be applied to the free end 25 of the bristles, causing the entire bristle tuft to move toward the proximal end, thereby creating—or increasing—a gap or separation 27 between the proximal end head portion 26 and the tuft retention ring 50. It can be appreciated that the gap 27 can also be achieved by pushing the tuft retention rings 50 in the opposite direction, such as pushing the tuft retention rings 50 toward the free end 25 of the bristles while the bristles stay in place. Referring to FIG. 6, in one embodiment, is a schematic representation of bristle tufts 21 inserted into retention rings 50, with a space 27 between the proximal end head portion 26 and the tuft retention ring 50. A force exerted on the free end 25 of the bristle tufts results in the space 27 being created, pursuant to this embodiment.

Figure 7:
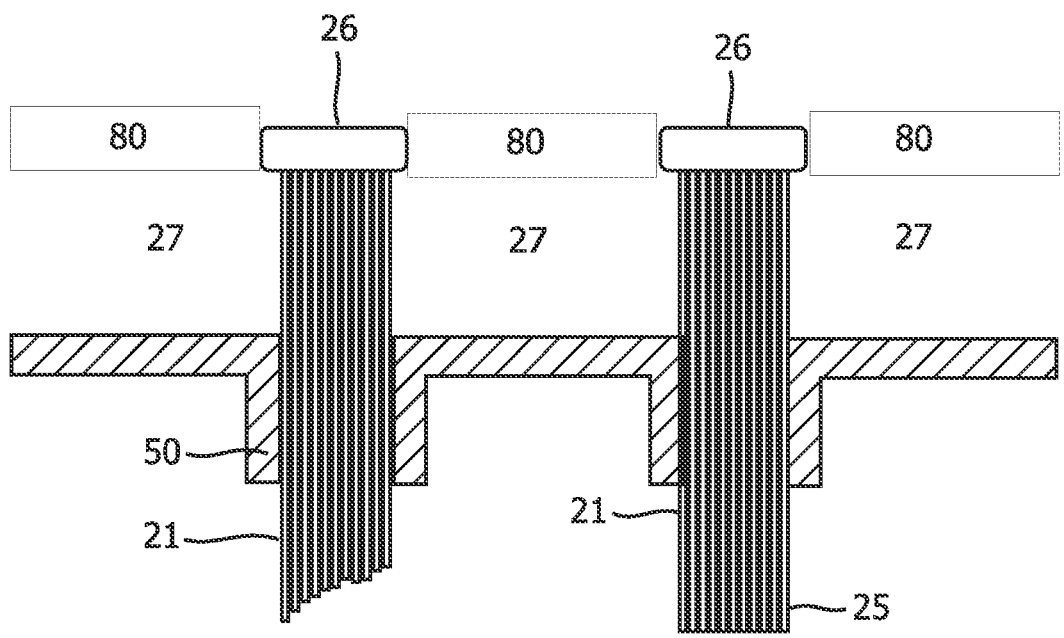
FIG. 7 is a schematic representation of a brush head during manufacturing, in accordance with an embodiment.

According to an embodiment, a guide 80 is utilized to create or control the location and/or size of the space or gap 27 created between the proximal end head portion 26 of each bristle tuft and the tuft retention ring 50 surrounding that bristle tuft. Referring to FIG. 7, in one embodiment, is a schematic representation of bristle tufts 21 inserted into optional retention rings 50, with one or more guides 80 positioning the proximal end head portion 26 of each bristle tuft into the proper location, thereby creating space 27. The one or more guides 80 can not only position the proximal end head portion 26 and bristle tuft relative to the retention ring, if one is present, but can also position bristle tufts relative to neighboring bristle tufts. Referring to FIG. 7, for example, the one or more guides 80 may exert a force on the bristle tufts, such as on the proximal end head portion 26 of the bristle tufts, in order to move the tufts to the proper position and/or hold the tufts in the proper position.

Figure 8:
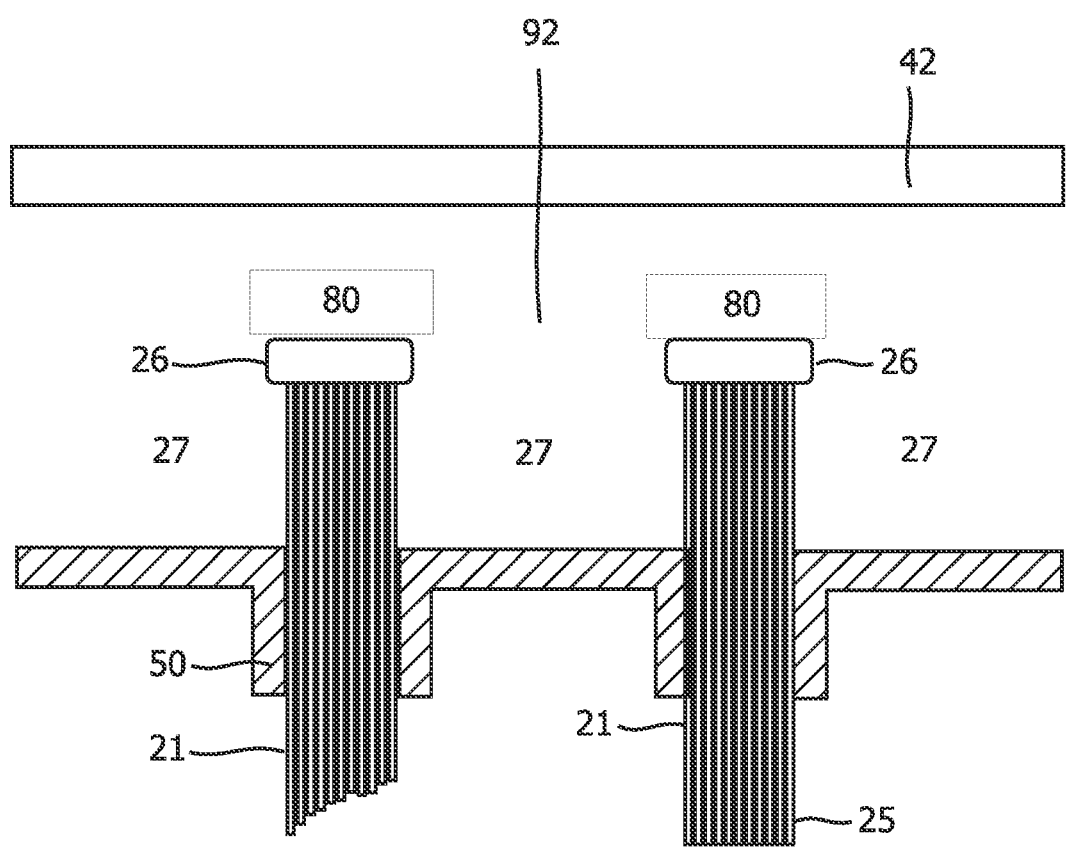
FIG. 8 is a schematic representation of a brush head during manufacturing, in accordance with an embodiment.

Referring to FIG. 8, in one embodiment, is a schematic representation of bristle tufts 21 inserted into optional retention rings 50, with one or more guides 80 positioning the proximal end head portion 26 of each bristle tuft into the proper location, thereby creating space 27. In this embodiment, the one or more guides 80 are positioned above the bristle tufts and engage the upper surface of the proximal end head portion 26 of each bristle tuft. The guide may be individual guides that interact with one or more tufts, or a single guide that interacts with all bristle tufts. The brush neck 42 may or may not be present at this stage. According to an embodiment, the guide 80 acts as a rotational guide to control rotation of the tuft. For example, if a circular tuft shape is utilized, it is possible for the bristle tuft and/or individual bristles to twist during the spacing step, and this will result in bristle and/or bristle tuft non-alignment. For example, the bristles may be splayed, and the trim profile of the brush can be significantly altered. The guide 80, therefore, may be configured to prevent rotation. If the bristle tuft is non-circular, an appropriately shaped guide can similarly be configured to prevent rotation of the non-circular bristle tufts.

According to an embodiment, guide 80 may be an external structure such as injection molding pin or part of the mold, and can be used to guide the tufts to the proper position. If the guide 80 is an external structure, however, a portion of the bristle tufts such as the proximal end head portion may be exposed when the elastomeric material is molded over the bristle tufts and retention rings if present. Accordingly, a secondary step may be required to mold the elastomeric material around the remainder of the bristle tufts.

Figure 9:
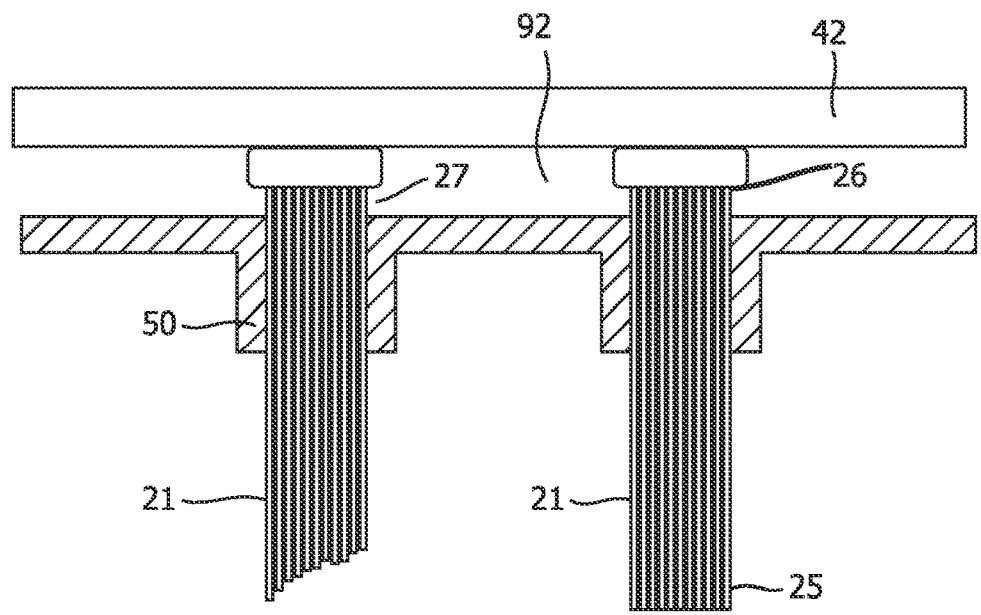
FIG. 9 is a schematic representation of a brush head during manufacturing, in accordance with an embodiment.

According to an embodiment, the brush neck 42 or another portion of the neck or head structure may act as the guide. Referring to FIG. 9, in one embodiment, is a schematic representation of bristle tufts 21 inserted into optional retention rings 50, with the brush neck 42 positioning the proximal end head portion 26 of each bristle tuft into the proper location, thereby creating space 27. With this configuration, a secondary molding step may not be necessary.

Figure 10:
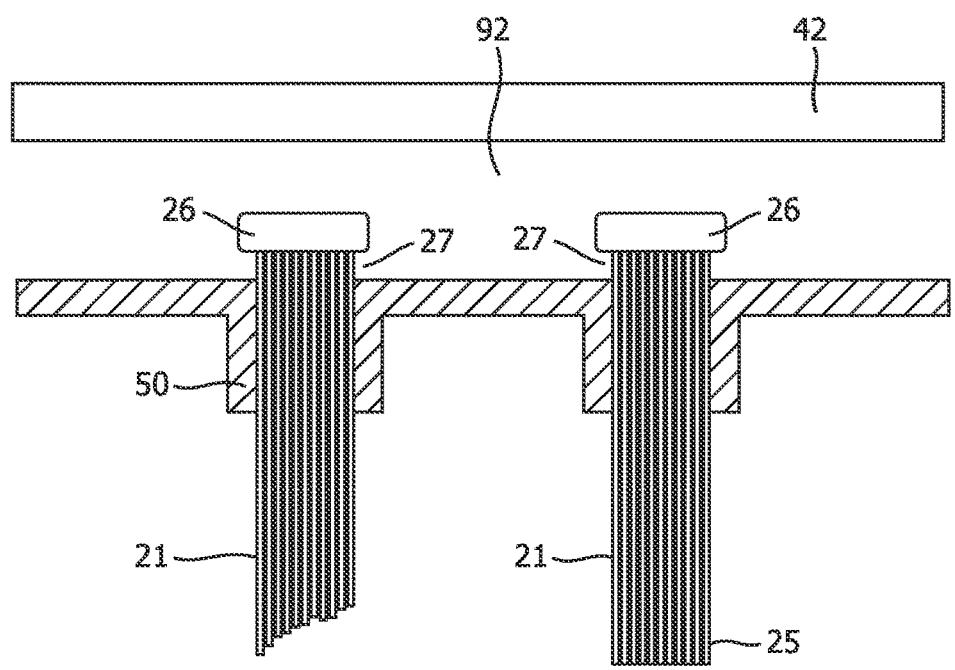
FIG. 10 is a schematic representation of a brush head during manufacturing, in accordance with an embodiment.

At step 250 of the method, the brush head neck 40 can be positioned to put the brush neck 42 in the proper location in relation to the retaining rings 50 and the bristle tufts 21, while maintaining the space 27. Referring to FIG. 10, in one embodiment, is a schematic representation of a portion of a brush head with the bristle tufts 21 inserted into retention rings 50, comprising a space 27 between the proximal end head portion 26 and the tuft retention ring 50. The brush neck 42 is positioned relative to the bristle tufts and retention rings such that a space 92 is created. Brush neck 42 can be properly positioned using a mold, for example, or other positioning mechanism. Notably, step 250 can be performed at any point during the method prior to step 260.

According to an embodiment, the hard brush neck 42 can be designed to promote fusing of the elastomeric matrix to the brush neck. For example, if the brush neck is made from materials such as Spandex®, PolyMeg®, or similar copolymers, this would allow fusing of the elastomer matrix to the brush neck, thereby increasing retention forces. In addition, this design provides additional flexibility to the bristle tuft within the brush neck, and therefore additional degrees of freedom of motion within the brush head. However, many other materials and configurations for the brush neck 42 are possible.

At step 260 of the method, an elastomeric material is molded over the brush neck 42, the head portion 26 of the bristle tufts, and the retaining rings 50, as well as the webbing links 91 if they are present. The molded elastomeric material forms an elastomeric matrix 30 that also fills in the space 92 between the brush neck 42 and the proximal end head portion 26, as well as the gap 27 between the proximal end head portion 26 and the retaining rings 50, as shown in FIG. 2. According to an embodiment, elastomeric matrix 30 is preferably made from a flexible thermoplastic elastomer.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A brush head comprising:
a hard neck having a brush neck;
a plurality of bristle tufts, each of which comprises a plurality of bristle strands having a free end and a proximal end, the proximal end comprising a proximal end head portion;
a plurality of retention rings, each configured to receive the proximal end of at least one of the plurality of bristle tufts; and,
an elastomeric matrix bonded to at least a portion of the brush neck, the plurality of retention rings, and the proximal end of the plurality of bristle tufts, wherein the proximal end head portion of each of the plurality of bristle tufts is configured to comprise a space between the proximal end head portion and the respective retention ring, and wherein the elastomeric matrix at least partially encompasses the brush neck, the plurality of retention rings, and the proximal end head portion of each of the plurality of bristle tufts.

2. The brush head of claim 1, wherein the plurality of retention rings is at least partially interconnected by a network of webbing.

3. The brush head of claim 2, wherein the network of webbing is at least partially encompassed within the elastomeric matrix.

4. The brush head of claim 1, wherein the elastomeric matrix completely encompasses the brush neck and the proximal end head portion of each of the plurality of bristle tufts.

5. The brush head of claim 1, wherein the bristle strands are made of nylon, and further wherein the elastomeric matrix comprises a flexible thermoplastic elastomer.

6. A method for manufacturing a brush head, the method comprising the steps of:
providing a plurality of retention rings and a plurality of bristle tufts, wherein each of the plurality of bristle tufts comprises a plurality of bristle strands having a free end and a proximal end;
inserting at least one of the plurality of bristle tufts into a respective one of the plurality of the retention rings;
applying heat to each of the bristle tuft proximal ends at a temperature and distance sufficient to at least partially melt the bristle tuft proximal end to create a proximal end head portion;
creating a first space between the each of the proximal end head portions and the respective retention ring;
positioning a brush neck in relation to the proximal end head portions, wherein the positioning of the brush neck defines a second space in relation to the proximal end head portions; and
injecting a thermoplastic elastomer to create an elastomeric matrix that at least partially encompasses the brush neck, the plurality of retention rings, and the proximal end head portions, wherein the elastomeric matrix fills the first and second spaces.

7. The method of claim 6, wherein said creating step comprises applying a force to the free end of each of the plurality of bristle tufts.

8. The method of claim 6, wherein said creating step comprises using a guide to create the first space.

9. The method of claim 6, wherein the plurality of retention rings are at least partially interconnected by a network of webbing.

10. The method of claim 6, wherein the elastomeric matrix completely encompasses the brush neck and the proximal end head portion of each of the plurality of bristle tufts.

11. The method of claim 6, wherein the bristles are made of nylon, and further wherein the elastomeric matrix is a flexible thermoplastic elastomer.

12. A brush head assembly for a power toothbrush, comprising:
a neck having a brush neck; and
a brush head, the brush head comprising:
a plurality of retention rings each containing a bristle tuft, each bristle tuft comprising a proximal end head portion at a proximal end thereof, the proximal end head portion separated from a respective one of the retention rings by a first space;
the brush neck positioned relative to the plurality of proximal end head portions to create a second space;
an elastomeric matrix at least partially encompassing the plurality of retention rings, the proximal end head portions, and the brush neck, wherein the elastomeric matrix fills the first and second spaces.

13. The brush head assembly of claim 12, wherein the plurality of retention rings is at least partially interconnected by a network of webbing.

14. The brush head assembly of claim 13, wherein the network of webbing is at least partially encompassed within the elastomeric matrix.

15. The brush head assembly of claim 12, wherein the elastomeric matrix completely encompasses the brush neck and the proximal end head portion of each of the plurality of bristle tufts.

* * * * *